(12) United States Patent
Xiong et al.

(10) Patent No.: US 11,389,182 B2
(45) Date of Patent: Jul. 19, 2022

(54) MICROELECTRONIC CONTROLLED MAGNETIC CLEANING SYSTEM AND METHOD THEREOF

(71) Applicants: CENTRAL SOUTH UNIVERSITY, Changsha (CN); THE SECOND XIANGYA HOSPITAL OF CENTRAL SOUTH UNIVERSITY, Changsha (CN)

(72) Inventors: Li Xiong, Changsha (CN); Siyuan Tang, Changsha (CN); Lezhi Li, Changsha (CN); Jiangjie Zhang, Changsha (CN)

(73) Assignees: CENTRAL SOUTH UNIVERSITY, Changsha (CN); THE SECOND XIANGYA HOSPITAL OF CENTRAL SOUTH UNIVERSITY, Changsha (CN)

( * ) Notice: Subject to any disclaimer, the term of this patent is extended or adjusted under 35 U.S.C. 154(b) by 272 days.

(21) Appl. No.: 16/607,245

(22) PCT Filed: Jan. 2, 2019

(86) PCT No.: PCT/CN2019/070112
§ 371 (c)(1),
(2) Date: Oct. 22, 2019

(87) PCT Pub. No.: WO2019/153984
PCT Pub. Date: Aug. 15, 2019

(65) Prior Publication Data
US 2020/0129191 A1     Apr. 30, 2020

(30) Foreign Application Priority Data

Feb. 12, 2018 (CN) .......................... 201810146691.4

(51) Int. Cl.
*A61B 17/22* (2006.01)
*A61B 34/00* (2016.01)
(Continued)

(52) U.S. Cl.
CPC ........ *A61B 17/22* (2013.01); *A61B 17/00234* (2013.01); *A61B 17/320758* (2013.01);
(Continued)

(58) Field of Classification Search
CPC .............. A61B 17/22; A61B 17/00234; A61B 17/320758; A61B 34/73;
(Continued)

(56) References Cited

U.S. PATENT DOCUMENTS

2004/0138677 A1* 7/2004 Little ................... A61B 17/221
   606/127
2008/0140100 A1* 6/2008 Gertner ................. A61B 17/22
   606/159

FOREIGN PATENT DOCUMENTS

| CN | 101450001 A | 6/2009 |
| CN | 103932764 A | 7/2014 |
| CN | 108186079 A | 6/2018 |

\* cited by examiner

*Primary Examiner* — Tan-Uyen T Ho
*Assistant Examiner* — Bridget E. Rabaglia
(74) *Attorney, Agent, or Firm* — Volpe Koenig

(57) ABSTRACT

A microelectronic controlled magnetic cleaning system, comprising a micron-scale fine line inner-end part, a micro-scale fine line outer motor control part, and a micro-scale fine line outer system electronic control part. The micron-scale fine line inner-end part is manufactured as a plurality of micron-scale magnetic fine lines, wherein the central magnetic fine lines are slightly wider than the periphery magnetic fine lines. The inner-end part of the central magnetic fine lines is spiral shaped. The micro-scale fine line outer motor control part is made by adding a high-precision (Continued)

micro-motor at the middle portion outside the central magnetic fine lines, When a larger obstruction is found by an endoscope or other optical device imaging system, the central magnetic fine lines can be controlled to arrive at a designated position, and motor speed can be controlled to clean the obstruction. Also disclosed is a micro-electronic controlled magnetic cleaning method.

3 Claims, 2 Drawing Sheets

(51) Int. Cl.
*A61B 17/00* (2006.01)
*A61B 17/3207* (2006.01)
(52) U.S. Cl.
CPC .... *A61B 34/73* (2016.02); *A61B 2017/00345* (2013.01); *A61B 2017/00411* (2013.01); *A61B 2017/00876* (2013.01); *A61B 2017/22072* (2013.01)
(58) Field of Classification Search
CPC .......... A61B 2017/00345; A61B 2017/00411; A61B 2017/00876; A61B 17/221; A61B 2017/2212; A61B 2017/22072
USPC ................ 606/127, 128, 159, 169, 9, 11, 12
See application file for complete search history.

MICROELECTRONIC CONTROLLED MAGNETIC CLEANING SYSTEM AND METHOD THEREOF

CROSS REFERENCE TO RELATED APPLICATIONS

This application is a 35 USC § 371 national stage of PCT/CN2019/070112, which was filed Jan. 2, 2019, claims priority to Chinese Application No. 201810146691.4, filed on Feb. 12, 2018, and is entitled "MICROELECTRONIC CONTROLLED MAGNETIC CLEANING SYSTEM AND METHOD THEREOF," both of which are incorporated herein by reference as if fully set forth.

FIELD OF THE INVENTION

The present disclosure relates to the field of electronic controlled magnetic technology, and more particularly relates to a microelectronic controlled magnetic cleaning system and a method thereof.

BACKGROUND OF THE INVENTION

An endoscope is an inspection instrument that integrates traditional optics, ergonomics, precision machinery, modern electronics, mathematics, software and the like. The endoscope is provided with an image sensor, an optical lens, a light source for illumination, a mechanical device and the like, and can enter the stomach through the oral cavity or enter the body through other natural orifices. The endoscope can be used to see lesions that cannot be displayed by X-rays, which is very useful for doctors. For example, a doctor can observe ulcers or tumors in the stomach with the help of the endoscope, and then makes an optimal therapy accordingly. During treatment, organs in the body need to be cleaned with the help of the endoscope and micro instrument equipment.

Most sets of traditional micro instrument equipment need to cooperate with a plurality of fiber fine line tools during obstruction removal and cleaning, with observations and operations for multiple times. However, the biggest problem is that the equipment needs to be replaced for multiple times, and the operation mode including breaking obstructions first and then cleaning them for multiple times is extremely cumbersome and complicated.

In view of the phenomenon that the obstruction removal and cleaning of the micro instrument equipment and related contactants is a big problem, in order to solve these shortcomings, to facilitate further promotion of rapid advancement and development of the endoscope and optical microscopic equipment, and to facilitate a mechanical engineer's learning about the relative positions between the micro instrument equipment and the related contactants thereof and deep structures of conduits in real time and visually during working of the endoscope and the optical microscopic equipment, the present disclosure provides a microelectronic controlled magnetic cleaning system.

SUMMARY OF THE INVENTION

In view of the above defects in the prior art, the technical problem to be solved by the present disclosure is to provide a microelectronic controlled magnetic cleaning system and a method thereof to solve the deficiencies of the prior art.

In order to achieve the above objective, the present disclosure provides a microelectronic controlled magnetic cleaning system, including:

a micron-scale fine line inner-end part, which is specifically manufactured as a plurality of micron-scale magnetic fine lines, wherein the central magnetic fine lines should be slightly wider than the periphery magnetic fine lines, and the inner-end part of the central magnetic fine lines should be spiral shaped;

a micron-scale fine line outer motor control part, which is specifically made by adding a high-precision micro-motor at the middle portion outside the central magnetic fine lines; when a larger obstruction is found by an endoscopic or other optical device imaging system, the central magnetic fine lines can be controlled to arrive at a designated position, and motor speed can be controlled to clean and remove the obstruction; and a micron-scale fine line outer system electronic control part, which is specifically used for: separating the wider, micron-scale, central magnetic fine lines from the narrower, micron-scale, periphery magnetic fine lines, connecting respectively the central and the periphery magnetic fine lines to an electromagnetic sensing system to ensuring that the control system can separately control the advancement and retraction and the magnetic properties of the central and the periphery magnetic fine lines, and combining with a gyroscope thermal tracking assistance system to locate the position of the micron-scale fine lines and to display the same in a digital imaging system.

Further, the gyroscope is a ten-axis gyroscope.

Further, the middle portions of the magnetic fine lines are wrapped with magnetic isolating materials.

A micro-electronic controlled magnetic cleaning method includes:

Step 1, starting an optical device imaging system, finding an obstruction existing in a conduit or a contactant, locating a relative position (x, y, z) of the obstruction by combining with a gyroscope thermal tracking assistance system, controlling a current direction such that the polarities of micron-scale central magnetic fine lines and periphery magnetic fine lines are opposite and then the micron-scale central magnetic fine lines and the periphery magnetic fine lines can attract each other, and pushing the tightly attracted micron-scale magnetic fine lines to the position (x, y, z) via the conduit;

Step 2, under the condition that the coordinates are known, controlling to change the current direction according to three-dimensional angle coordinates acquired by a gyroscope to change the magnetic pole of the micron-scale central magnetic fine lines such that the polarities of the micron-scale central magnetic fine lines and the periphery magnetic fine lines are the same and then the micron-scale central magnetic fine lines and the periphery magnetic fine lines can repel each other, pushing the micron-scale periphery magnetic fine lines for several microns such that the periphery magnetic fine lines wrap the obstruction, and then changing the current direction to negate the magnetic pole of the micron-scale central magnetic fine lines such that the polarities of the micron-scale central magnetic fine lines and the periphery magnetic fine lines are opposite and then the micron-scale central magnetic fine lines and the periphery magnetic fine lines can attract the obstruction;

Step 3, controlling an external electronic control system to take out the obstruction;

Step 4, repeating the steps 1, 2 and 3 for several times to take out the related obstructions in the conduit or contactant one by one;

Step 5, if the found obstruction is larger in size, controlling a motor to make the micron-scale central magnetic fine lines rotate first, and then breaking the obstruction by utilizing a high-speed rotating torque force.

The present disclosure has the beneficial effects that:

the present disclosure is convenient to operate and relatively high in efficiency, and may promote rapid advancement and development of the endoscope and optical microscopic equipment, and a mechanical engineer can conveniently learn about the relative positions between micro instrument equipment and the related contactants thereof and deep structures of conduits in real time and visually during working of the endoscope and the optical microscopic equipment.

The concept, the specific structure and generated technical effects of the present disclosure will be further described in conjunction with the accompanying drawings in order to fully understand the objects, features and effects of the present disclosure.

DETAILED DESCRIPTION OF THE EMBODIMENTS

Embodiment I

Figure 1:
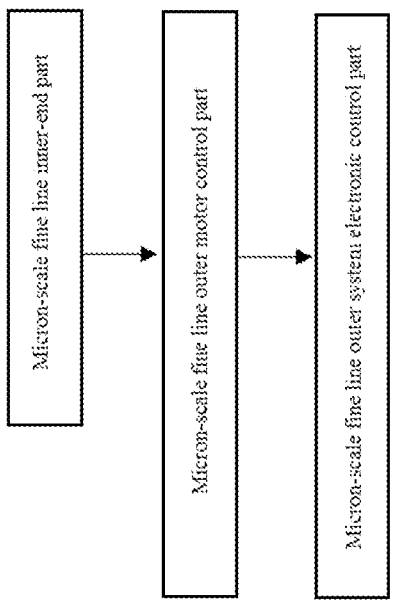
FIG. 1 is a structural block diagram of the present disclosure.

As shown in FIG. 1, a microelectronic controlled magnetic cleaning system includes:

a micron-scale fine line inner-end part (1), which is specifically manufactured as a plurality of micron-scale magnetic fine lines, wherein the central magnetic fine lines (11) should be slightly wider than the periphery magnetic fine lines (12). The inner-end part of the central magnetic fine lines (11) should be spiral shaped; the middle portions of all the magnetic fine lines are wrapped with magnetic isolating materials to ensure that only the tip portions of the inner ends of the magnetic fine lines may accept electromagnetic sensing;

a micron-scale fine line outer motor control part (2), which is specifically made by: adding a high-precision micro-motor at the middle portion outside the central magnetic fine lines (11); when a larger obstruction is found by an endoscopic or other optical device imaging system, the central magnetic fine lines (11) can be controlled to arrive at a designated position, and motor speed can be controlled to clean and remove the obstruction; and a micron-scale fine line outer system electronic control part (3), which is specifically used for: separating the wider, micron-scale, central magnetic fine lines (11) from the narrower, micron-scale, periphery magnetic fine lines (12), connecting respectively the central and the periphery magnetic fine lines to an electromagnetic sensing system to ensuring that the control system can separately control the advancement and retraction and the magnetic properties of the central and the periphery magnetic fine lines, and combining with a gyroscope thermal tracking assistance system to locate the position of the micron-scale fine lines and to display the same in a digital imaging system.

In addition, the gyroscope is a ten-axis gyroscope.

Figure 2:
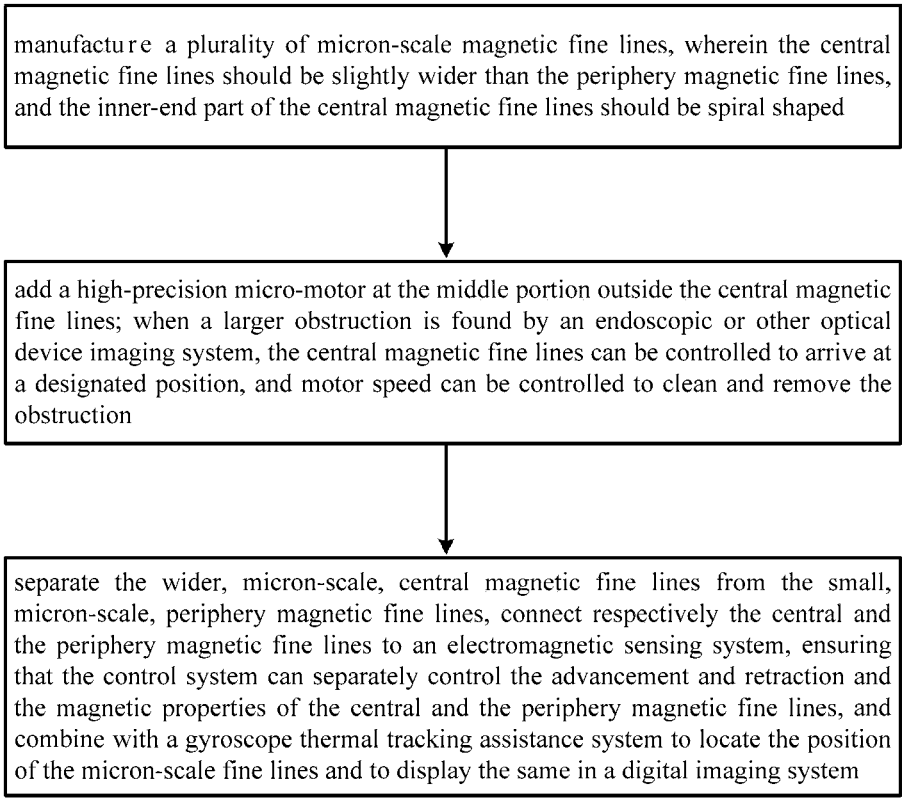
FIG. 2 is a flow chart of the present disclosure.

As shown in FIG. 2, a micro-electronic controlled magnetic cleaning method includes that: Step 1, an optical device imaging system is started, an obstruction existing in a conduit or a contactant is found, a relative position (x, y, z) of the obstruction is located by combining with a gyroscope thermal tracking assistance system, a current direction is controlled such that the polarities of micron-scale central magnetic fine lines and periphery magnetic fine lines are opposite and then the micron-scale central magnetic fine lines and the periphery magnetic fine lines can attract each other, and the tightly attracted micron-scale magnetic fine lines are pushed to the position (x, y, z) via the conduit.

Step 2, under the condition that the coordinates are known, the current direction is controlled to change according to three-dimensional angle coordinates acquired by a gyroscope to change the magnetic pole of the micron-scale central magnetic fine lines, such that the polarities of the micron-scale central magnetic fine lines and the periphery magnetic fine lines are the same and then the micron-scale central magnetic fine lines and the periphery magnetic fine lines can repel each other. The micron-scale periphery magnetic fine lines are pushed for several microns such that the periphery magnetic fine lines wrap the obstruction, and then the current direction is changed to negate the magnetic pole of the micron-scale central magnetic fine lines such that the polarities of the micron-scale central magnetic fine lines and the periphery magnetic fine lines are opposite and then the micron-scale central magnetic fine lines and the periphery magnetic fine lines can attract the obstruction.

Step 3, an outer electronic control system is controlled to take out the obstruction;

Step 4, the steps 1, 2 and 3 are repeated for several times to take out the related obstructions in the conduit or contactant one by one;

Step 5, if the found obstruction is larger in size, a motor is controlled to make the micron-scale central magnetic fine lines rotate first, and then the obstruction is broken by a high-speed rotating torque force.

Embodiment II

Figure 3:
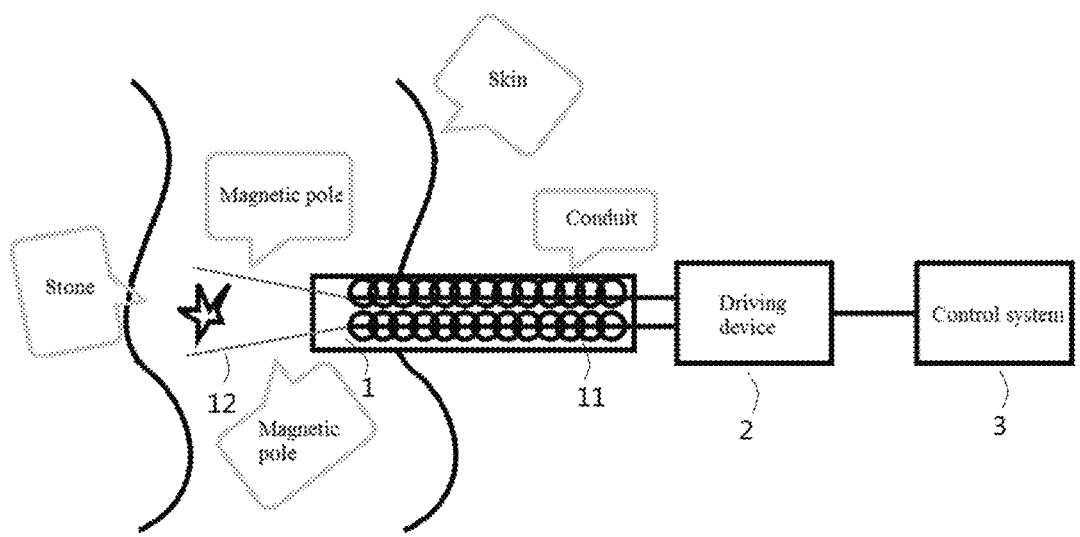
FIG. 3 is a structural schematic diagram of an embodiment of the present disclosure.

A difference from Embodiment 1 is that an operation for breaking the obstruction (a stone as shown in FIG. 3) also needs to be added into the system. If the found obstruction is larger in size, the motor is controlled first to make the micron-scale central magnetic fine lines rotate, and the obstruction is broken by a high-speed rotating torque force. Since the periphery magnetic fine lines have wrapped the obstruction, injury to the contactant or conduit due to breaking of the obstruction may be further reduced, and scattering of the broken obstructions may be reduced to a large extent. In addition, due to the design of an electronic control system, the mechanical engineer may not only control the current direction to change the electromagnetic polarity, but also control the size of a current to change the size of a magnetic force, so as to grab obstructions in different masses. Meanwhile, the motor speed and the force may be both controlled by the system. After the operations of an established basic line are completed, a next operation is performed if it is necessary to search a next obstruction. Similarly, the first and second steps are continued to complete subsequent implementation steps, and a new operation line is replanned. The position of the obstruction and an electronic control current, a rotating speed and the like of an instrument are finely corrected, and then the subsequent operations are performed.

It is worth mentioning that an operated object needs to be systematically estimated before the use of the system. The simplest and most practical mode is that the mechanical engineer measures a safe voltage and a safe current of the contactant first, and had better evaluate the elements, the mass, the volume and the like of the obstruction as well, so as to ensure that the obstruction may be broken under the action of the torque force of the motor and ensure that the micron-scale fine line system has an enough magnetic force to take out the obstruction. Moreover, the mechanical engineer should also learn to finely adjust some parameters and the like by his/her own during use, so as to facilitate a contrast operation. The parameters include the size of a current, the motor speed and the like.

The specific embodiments of the present disclosure are described above in detail. It should be understood that those of ordinary skill in the art can make many modifications and variations in accordance with the concept of the present disclosure without creative work. Therefore, any technical solutions that can be obtained by a person skilled in the art based on the prior art by logic analysis, reasoning or limited experimentation should all fall within the protection scope defined by the claims.

The invention claimed is:

1. A microelectronic controlled magnetic cleaning system, comprising:
   a micron-scale fine line inner-end part, which comprises a plurality of micron-scale magnetic fine lines, wherein central magnetic fine lines are wider than periphery magnetic fine lines, and an inner-end part of the central magnetic fine lines are spiral shaped;
   a micro-scale fine line outer motor control part, which comprises a high-precision micro-motor located at the outer middle of the central magnetic fine lines; when a larger obstruction is found by an endoscopic or other optical device imaging system, the central magnetic fine lines can be controlled to arrive at a designated position, and a motor speed can be controlled to clean and remove the obstruction; and
   a micro-scale fine line outer system electronic control part, which comprises a gyroscope thermal tracking assistance system, the micro-scale fine line outer system electronic control part is used for: separating the wider, micron-scale, central magnetic fine lines from the narrower, micron-scale, periphery magnetic fine lines, connecting respectively the central and the periphery magnetic fine lines to an electromagnetic sensing system to ensure that the control system can separately control the advancement and retraction and the magnetic properties of the central and the periphery magnetic fine lines, and combining with the gyroscope thermal tracking assistance system to locate the position of the micron-scale fine lines and to display the same in a digital imaging system,
   wherein the gyroscope thermal tracking assistance system comprises a gyroscope.

2. The microelectronic controlled magnetic cleaning system according to claim 1, wherein the gyroscope is a ten-axis gyroscope.

3. The microelectronic controlled magnetic cleaning system according to claim 1, wherein the middle portions of the magnetic fine lines are wrapped with magnetic isolating materials.

* * * * *